United States Patent [19]

Lang et al.

[11] 4,172,639

[45] Oct. 30, 1979

[54] APPARATUS FOR DETERMINATION OF CORNEAL ASTIGMATISM

[75] Inventors: Walter Lang; Ortwin Mueller, both of Koenigsbronn, Fed. Rep. of Germany

[73] Assignee: Carl Zeiss Stiftung, Oberkochen, Germany

[21] Appl. No.: 835,193

[22] Filed: Sep. 21, 1977

[30] Foreign Application Priority Data

Sep. 25, 1976 [DE] Fed. Rep. of Germany ....... 2643344

[51] Int. Cl.² .............................................. A61B 3/10
[52] U.S. Cl. ................................................... 351/13
[58] Field of Search ..................... 351/13, 12; 356/124

[56] References Cited

U.S. PATENT DOCUMENTS

| | | | |
|---|---|---|---|
| 1,774,832 | 9/1930 | Keeler | 351/12 |
| 3,482,904 | 12/1969 | Volk | 351/13 |
| 3,542,458 | 11/1970 | Volk | 351/13 X |
| 3,598,478 | 8/1971 | Townsley | 351/13 X |
| 3,797,921 | 3/1974 | Kilmer et al. | 351/13 X |
| 4,046,463 | 9/1977 | LaRussa et al. | 351/13 |

*Primary Examiner*—Paul A. Sacher

*Attorney, Agent, or Firm*—Stonebraker, Shepard & Stephens

[57] ABSTRACT

Apparatus for use with an operating microscope employed in observing the cornea of the human eye, for example in connection with cornea transplant operations. A plexiglass tube surrounds the objective of the microscope and is fed with light from a suitable source, so that an image of the circular illuminated lower end of the plexiglass tube is reflected by the cornea of the patient back into the microscope and is observed by the person using the microscope. The character and extent of distortion of the reflected image is an indication of the corneal astigmatism. The eyepiece of the microscope is provided with a reticle in connection with which the reflected image is observed. In one form of the invention, the recticle has diametrical crossed lines and concentric circular lines. In other form of the invention the recticle has a diametrically extending linear scale, and is used in connection with an eyepiece attachment having means for rotating the recticle to align the linear scale with any desired axis of the reflected image and micrometer means for moving a pointer to measure the length of the reflected image along such axis.

3 Claims, 5 Drawing Figures

APPARATUS FOR DETERMINATION OF CORNEAL ASTIGMATISM

BACKGROUND OF THE INVENTION

This invention relates to apparatus for use in combination with an operating microscope for the qualitative, semi-quantitative, and quantitative determination of corneal astigmatism of the human eye.

In performing corneal transplants on the human eye, the calotte-shaped transplant of the donor eye is sewn to the adjoining cornea of the receiving eye by very fine suture material having a diameter of about 0.02 millimeters. This delicate operation is possible only with the use of an operating microscope which provides the operator with a three-dimensional true-color image as a magnifying aid in observing the site of the operation.

A difficulty of these operations resides in the fact that, even with extremely careful suturing, the pull exerted by the thread on the transplant is not distributed uniformly. An undesired deformation of the cornea is produced as a result of the differential pull of the thread on the transplant, this undesired deformation being referred to as corneal astigmatism. The corneal astigmatism produced in this way may have a value up to about seven diopters. During the course of healing and cicatrization, the corneal astigmatism which has been unintentionally introduced as a result of the operation can usually be reduced by up to about two diopters, but usually not more than this reduction is possible. Ordinarily the residual astigmatism which can be tolerated is not more than two diopters. If the reduction of the astigmatism during healing can be not more than about two diopters and if the tolerable limit of residual astigmatism is not more than about two diopters, this means that the initial astigmatism unintentionally introduced by the suturing operation should be not more than four diopters, whereas experience shows that it is frequently more than this. Therefore it becomes vitally important to check the astigmatism of the cornea at the very moment that the suturing is being accomplished, in order to make sure that the suturing does not introduce too great an amount of astigmatism, and to be able to take immediate corrective action if it is found that too great an amount is introduced. The present invention provides simple and effective means for accomplishing this checking of corneal astigmatism at the time that the transplant operation is in progress.

THE PRIOR ART

In order to determine the position of the axes of the two principal sections and the diopter value of the astigmatism, it is already known to use an ophthalmometer. However, because of their geometrical dimensions, the known ophthalmometers cannot be used in combination with an operating microscope, and are not suitable for routine clinical operation.

There is a known instrument called a keratoscope or photokeratoscope which permits a qualitative or semi-quantitative evaluation of corneal astigmatism. However, the precision obtainable with these simple instruments is not sufficient for the surgeon.

For the precise measurement of corneal astigmatism, there is also an instrument in which a Wollaston prism, arranged in a modified operating microscope, is used in order to make the image twice as large. However, this arrangement requires a change in the construction of the operating microscope, and also impairs the quality of the image in the microscope, so that it does not provide a satisfactory solution for the task of checking and measuring astigmatism during the actual corneal transplantation operation.

Another known instrument for measuring corneal astigmatism during the operation is based on coupling a television unit with an operating microscope and an evaluation device. This instrument is extremely expensive.

SUMMARY OF THE INVENTION

The object of the present invention is to provide apparatus for determination of corneal astigmatism during the progress of a transplant operation, which apparatus on the one hand avoids the extremely high expense of certain of the prior art devices, and on the other hand avoids the impairment of the image or other functioning of the microscope, as is done by other devices of the prior art.

Another object is the provision of such apparatus so designed that it may be used on conventional existing operation microscopes without altering the construction of such microscopes, and so designed as to permit the qualitative, semiquantitative, and quantitative determination of corneal astigmatism during the corneal transplantation operation.

These objects are attained, in accordance with the invention, by using a ring shaped plexiglass rod (that is, a plexiglass tube) arranged around the main objective lens of the operating microscope, the plexiglass tube being illuminated by light from two optical light guides. A reticle is provided in one of the two eyepieces of the binocular operating microscope, and the second eyepiece of the microscope is developed as an ocular micrometer.

With such apparatus, the reflected image, observed through the operating microscope, of the illuminated circular end of the plexiglass tube, as reflected from the cornea, permits a qualitative determination as to the presence of astigmatism, since in such a case the reflected image of the circular end of the tube is elliptically deformed. The reticle with concentric rings and the system of cross lines which is arranged in one of the two eyepieces of the operating microscope permits a semi-quantitative determination of the astigmatism.

The reticle can be arranged in a fixed position in the eyepiece of the microscope. It is also possible, and within the scope of the invention, to arrange the reticle in a movable manner so that it may be displaced laterally into and out of the field of view of the eyepiece, by mounting the reticle on a simple rectilinear slide, or on a pivoted member mounted to swing on a pivot axis parallel to and offset from the optical axis of the eyepiece. A mirror arrangement may also be used, to reflect an image of the reticle into the field of view of the eyepiece when desired, the mirror being movable to remove the reticle image from the field of view when it is not desired, to enable the surgeon to view the operating field without the disturbing lines and circles of the reticle.

In one advantageous embodiment of the apparatus of the invention, the ocular micrometer is provided with coincidence matching and internal reading.

A particular advantage of the invention resides in the fact that it is possible, with simple means and at little expense, to determine corneal astigmatism qualitatively as well as semi-quantitatively and quantitatively during a corneal transplantation. In addition to this, the apparatus in accordance with the invention can be connected in a simple and rapid manner to an operating microscope, without impairing the operation of the operating microscope. Moreover, it can be applied subsequently to an existing operating microscope without any change in construction.

An illustrative preferred embodiment of the invention is illustrated in the drawings and will be described in further detail below.

DETAILED DESCRIPTION

The present invention is used with a conventional operation microscope as customarily employed by a surgeon during the performance of a corneal transplantation operation on a human eye. Such operation microscopes having two eyepieces so as to give a binocular or three-dimensional field of view, are well known in the art and so it is unnecessary to illustrate the microscope itself. The illustration in the present drawings, although somewhat schematic, will be sufficient, in connection with the description, to enable those skilled in this art and familiar with such microscopes to understand and practice the invention.

Figure 1:
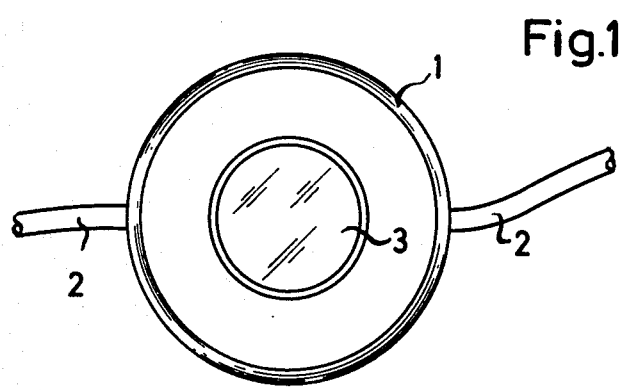
FIG. 1 is a schematic endwise view of the main objective lens of the operating microscope as seen from the eye of the patient, illustrating the plexiglass rod around the objective.

The main objective lens of the microscope is illustrated schematically at 3 in FIG. 1, viewed as seen from the eye of the patient. Surrounding this objective 3, and held rigidly with relation to the objective by any suitable holding means, is a length of circular cylindrical plexiglass tubing shown at 1, supplied with light at two or more points as by means of fiber optics bundles illustrated schematically at 2, receiving light from any suitable source of light which may be a controlled source whereby the intensity of light may be adjusted or regulated.

Because of the illumination of the plexiglass tube 1, the circular lower end of this tube will be illuminated, and the image of this circle will be reflected by the cornea of the patient, the reflected image being observed in the microscope. If the cornea being observed is free from astigmatism, the reflected image of the illuminated circular end of the tube 1 will be a perfect circle. However, if astigmatism is present in the cornea being observed, the reflected image of the circle will be deformed into an ellipse, the eccentricity of the ellipse being in proportion to the degree of astigmatism.

Figure 2:
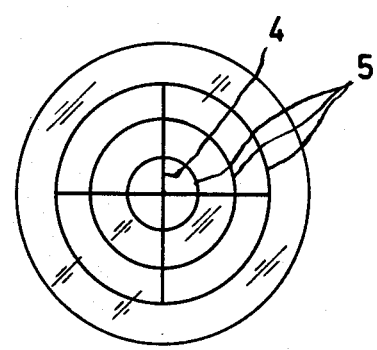
FIG. 2 is a face view of the reticle arranged in one eyepiece of the microscope.

In one eyepiece of the microscope there is placed a reticle such as shown in FIG. 2. This reticle preferably has crossed diametrical lines 4 and concentric circular lines or rings 5. By observing the degree of eccentricity of the reflected image of the circular end of the illuminated tube 1, as reflected by the cornea and falling upon the reticle in the eyepiece, with relation to the markings on the reticle, the surgeon can estimate the amount of deformation of the reflected image from a true circle, and thus can obtain a semi-quantitative determination of the corneal astigmatism.

As already mentioned above, it is not necessary that this reticle be placed permanently in the eyepiece of the microscope. The recticle can be mounted on a sliding or swinging mount to move laterally into and out of the field of view of the eyepiece, so that when not making an observation of astigmatism, the surgeon may move the reticle aside, so that his field of view of the cornea, during the transplant operation, will not be hampered or obstructed by the lines on the reticle.

Figure 3:
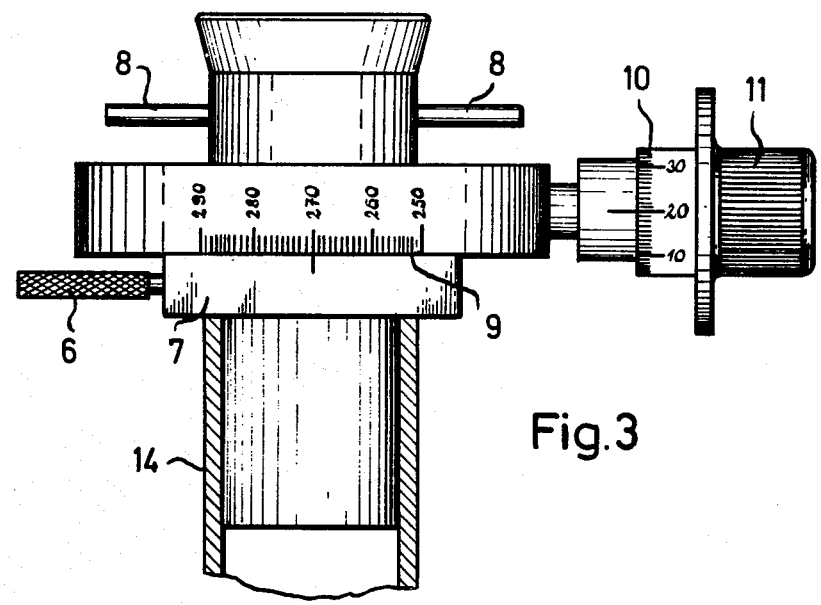
FIG. 3 is a view partly in side elevation and partly in section, illustrating the screw micrometer on one eyepiece of the microscope.
Figure 4:
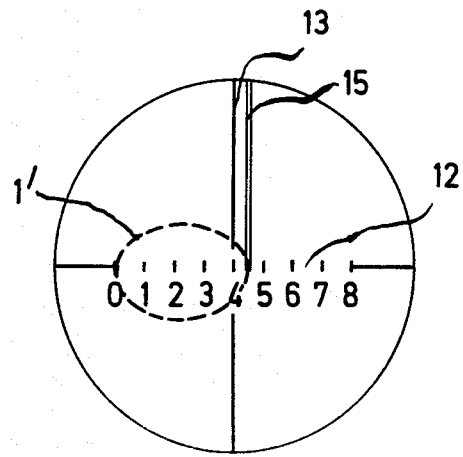
FIG. 4 is an illustration of the field of view of the ocular screw micrometer of FIG. 3.

FIGS. 3 and 4 illustrate an arrangement which may be used either as a substitute for or as a supplement to the reticle shown in FIG. 2.

In FIG. 3, the eyepiece support 14 of the operating microscope carries a screw micrometer supported by an annular body 7 encircling and clamped to the eyepiece support 14 by means of the knurled screw 6. An index mark is placed on this annular support 7, as shown, for reading a scale 9 graduated in degrees and marked on the rotatable body of the micrometer, just above the support 7. For rotating this body, it is provided with radial handles 8 which are removable for easy sterilization, so that when the surgeon grasps the handles to turn the micrometer, he touches only sterilized parts.

Within the rotatable body of the micrometer there is a reticle illustrated in FIG. 4, having a diametrically extending graduated scale 12 with linear graduations, and a diametrical cross line 13 perpendicular to the diametrical scale 12. A pointer 15 can be displaced in the direction of the linear scale 12 by turning the micrometer screw by means of the handle having a sterilizable sleeve 11 surrounding it, and a micrometer scale 10 enables an exact reading of the extent of displacement of the pointer 15, to intervals or increments finer than the graduations of the scale 12.

When using this arrangement for the accurate quantitative determination of corneal astigmatism, the ocular screw micrometer is first of all turned by means of the sterilized pins 8 until one principal axis of the elliptical image 1' of the luminous ring 1, as reflected from the cornea of the patient, and as shown schematically in FIG. 4, coincides with the direction of the linear graduation 12. Then the image 1' is placed in such a position that one vertex of the ellipse coincides with the zero point of the scale 12. The mark 15 is then shifted, by turning the sterilized handle 11, until it coincides with the other vertex of the ellipse or limits it. The length of the principal axis of the ellipse 1' can then be read from the scale 12 and the scale 10. After this measurement, the micrometer is turned by means of the handles 8, through approximately 90°, until the other principal axis of the elliptical image 1' lies on the linear scale 12. The measurement is then repeated. The value of the corneal astigmatism can be determined quantitatively with great accuracy, from the lengths of the two principal axes of the elliptical image 1', that is, the image of the circular illuminated tube 1 as reflected by the astigmatic cornea into the microscope.

Thus it is seen that using the screw micrometer arrangement of FIGS. 3 and 4, together with the illuminated tube of FIG. 1, a very accurate or precise quantitative determination of the amount of astigmatism may be obtained, at the time of performing the transplant operation, and any necessary corrective steps can be immediately taken. Using the reticle of FIG. 2 in conjunction with the illuminated plexiglass tube of FIG. 1, without the equipment of FIGS. 3 and 4, the existence of astigmatism can be determined and an approximation of the extent thereof or what may be called a semi-quantitative determination of astigmatism may be obtained.

Figure 5:
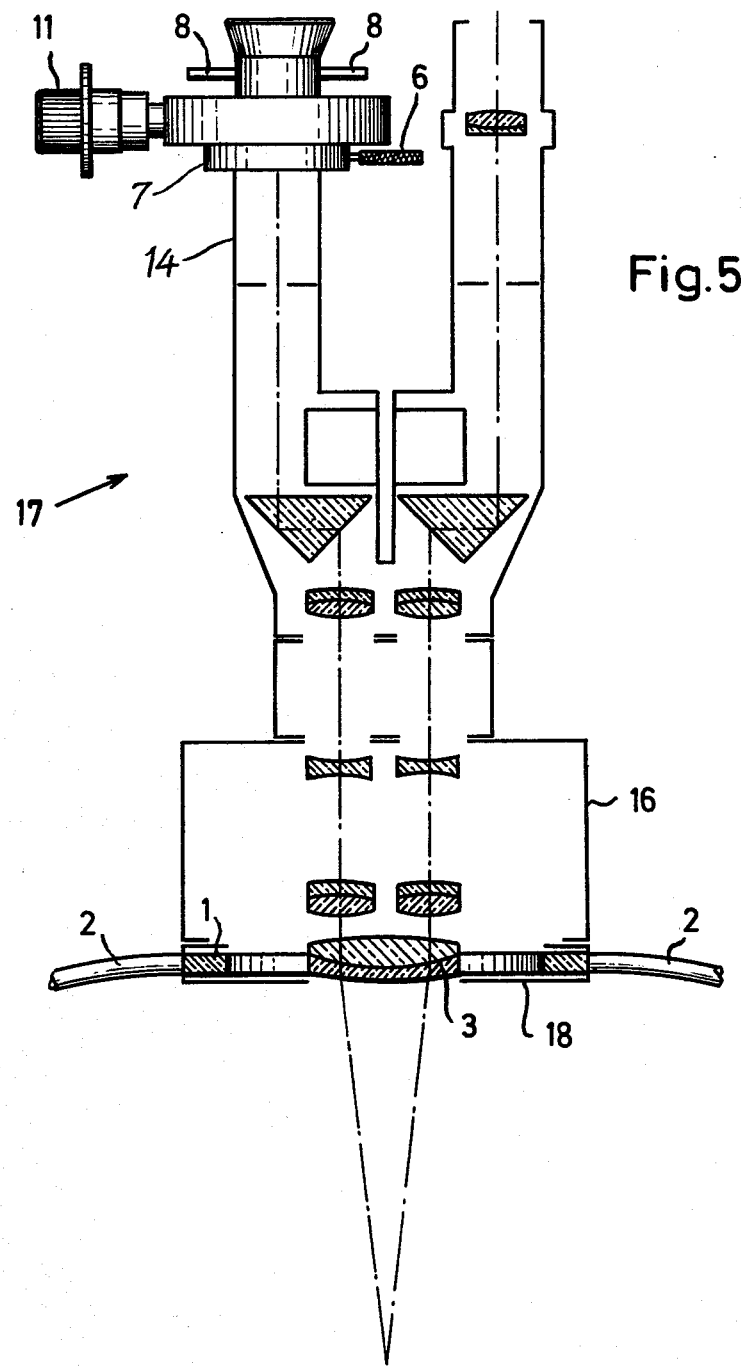
FIG. 5 is a schematic vertical section through a conventional operation microscope illustrating the present invention applied thereto.

Referring to FIG. 5, a conventional binocular operation microscope, as well known in the art, is shown schematically in outline form in FIG. 5. The parts illustrated and described in detail in connection with FIG. 3 are here shown in FIG. 5 in the normal position of use applied to one of the two eyepieces of the microscope which is indicated in general at 17. The parts illustrated and described in detail in connection with FIGS. 1 and 2 of the drawings are here shown in FIG. 5 in the normal position of use in surrounding relation to the objective 3 of the microscope, located preferably in a supplementary housing 18 detachably mounted on the nose piece 16 of the microscope.

What is claimed is:

1. Apparatus for use in combination with an operation microscope having an objective lens and two eyepieces for determination of corneal astigmatism of the human eye, said apparatus comprising a circular plexiglass tube surrounding and concentric with said objective, light guide means for conveying light to said plexiglass tube, a reticle associated with one of said eyepieces of said microscope in such position that the image of said plexiglass tube reflected by the cornea back into the microscope may be observed with relation to said reticle, and an ocular micrometer mounted on the other of said eyepieces.

2. Apparatus as defined in claim 1, wherein said reticle is marked with diametrical cross lines perpendicular to each other and with a plurality of concentric circles radially spaced from each other.

3. Apparatus as defined in claim 1, wherein said reticle is marked with a graduated scale extending diametrically across said reticle.

* * * * *